US009242278B1

(12) United States Patent
Chun et al.

(10) Patent No.: US 9,242,278 B1
(45) Date of Patent: Jan. 26, 2016

(54) EFFECTIVE SOUND GENERATOR USING PULSED THERMAL RADIATION

(71) Applicant: JEJU NATIONAL UNIVERSITY INDUSTRY-ACADEMIC COOPERATION FOUNDATION, Jeju-si, Jeju-do (KR)

(72) Inventors: Wongee Chun, Jeju-si (KR); Seungjin Oh, Jeju-si (KR); Namjin Kim, Jeju-si (KR); Youncheol Park, Jeju-si (KR); Yeongmin Kim, Seogwipo-si (KR); Kuan Chen, Salt Lake City, UT (US)

(73) Assignee: Jeju National University Industry-Academic Cooperation Foundation, Jeju-si, Jeju-do (KR)

( * ) Notice: Subject to any disclaimer, the term of this patent is extended or adjusted under 35 U.S.C. 154(b) by 0 days.

(21) Appl. No.: 14/471,681

(22) Filed: Aug. 28, 2014

(30) Foreign Application Priority Data

Aug. 28, 2014 (KR) ........................ 10-2014-0113013

(51) Int. Cl.
*A61M 15/00* (2006.01)
*B08B 3/00* (2006.01)

(52) U.S. Cl.
CPC ........................................ *B08B 3/00* (2013.01)

(58) Field of Classification Search
CPC .............. A61L 2/00; B08B 3/12; B08B 5/04; B08B 7/028; F41G 3/22; H04R 17/00
USPC ........... 166/177.1; 128/200.14; 422/127–128; 181/106; 73/152.05
See application file for complete search history.

(56) References Cited

U.S. PATENT DOCUMENTS

2008/0253010 A1* 10/2008 Cruz ........................ F24J 2/067 359/885

FOREIGN PATENT DOCUMENTS

KR 10-207380 * 12/2012 ............. G01K 15/04

OTHER PUBLICATIONS

Korean Patent Office Machine English Translation of KR 10-207380.*

* cited by examiner

*Primary Examiner* — Monzer R Chorbaji
(74) *Attorney, Agent, or Firm* — Novick, Kim & Lee, PLLC; Jae Youn Kim

(57) ABSTRACT

Disclosed herein is a high-efficiency acoustic wave generator using a pulsed thermal radiation beam. The generator is configured such that when a pulse beam formed by a light interrupter is directly radiated onto a porous material having a woven net or steel scrubber shape, thin wires of the porous material repeatedly rapidly thermally-expand and contract, whereby air in the space between the wires is momentarily heated and cooled, and the expansion and contraction of air is directly transmitted to an air column formed just adjacent to the porous material. By virtue of the above structure, the efficiency of the generator is markedly improved compared to the conventional technique, and the productivity is also greatly enhanced.

3 Claims, 2 Drawing Sheets

EFFECTIVE SOUND GENERATOR USING PULSED THERMAL RADIATION

BACKGROUND OF THE INVENTION

1. Field of the Invention

The present invention relates generally to acoustic wave generators and, more particularly, to a high-frequency acoustic wave generator using a pulsed thermal radiation beam that is configured such that when a pulse beam formed by a light interrupter is directly radiated onto a porous material having a woven net or steel scrubber shape, thin wires of the porous material repeatedly rapidly thermally-expand and contract, whereby air in the space between the wires is momentarily heated and cooled, and the expansion and contraction of air is directly transmitted to an air column formed just adjacent to the porous material. By virtue of the above structure, the efficiency of the generator according to the present invention is markedly improved compared to the conventional technique, and the productivity is also greatly enhanced.

The present invention is configured to generate high-frequency (ultrasonic) waves from obtained acoustic waves and provide the acoustic waves to a variety of industrial fields including fields pertaining to sterilization, washing, etc.

2. Description of the Related Art

Generally, solar energy is used for air-conditioning or heating of buildings, lighting devices or power generation.

With regard to this, over the past half century studies on solar energy have been continuously conducted and many related techniques have already been commercialized. At present, various forms of solar energy conversion systems for improvement in efficiency are under study.

Meanwhile, the conversion of solar energy into acoustic energy, along with a solar tracking system, is opening a new chapter in technology using high-density solar energy. Most of this technology is focused on the development of thermoacoustic refrigerators.

Conventional thermoacoustic wave generators using solar light are configured such that a porous stack (solid block) is disposed in a transparent tube closed on one end thereof and thermoacoustic waves are generated by heating a portion thereof adjacent to the closed end of the transparent tube.

However, in conventional thermoacoustic wave generators, to generate high-frequency thermoacoustic waves, the size of the transparent tube must be reduced inversely proportional to the frequency of thermoacoustic waves, and a high thermal gradient between both ends of the porous stack must be maintained. Therefore, in practice it is very difficult to embody such conventional thermoacoustic wave generators. Referring to the result of research so far, it has been reported that the University of Utah, USA succeeded in producing a maximum acoustic wave of 3 kHz via this conventional technique.

In other words, it is no exaggeration to say that it is almost impossible to produce thermoacoustic waves in an ultrasonic wave range of 18 kHz or more using the above conventional technique.

Furthermore, research on generating thermoacoustic waves has focused on generating compression waves via a process of heating a very small micro-sized structure by momentarily applying Joule's heat resulting from electric energy to the structure and then cooling the structure. This process is repeated so that air surrounding the structure is expanded and cooled.

In an effort to overcome the problems of the conventional techniques pertaining to thermoacoustic wave generators, the applicant of the present invention proposed a thin metal plate membrane structure in Korean Patent Registration No. 10-1207380.

However, the technique of No. 10-1207380 is problematic in that the efficiency in producing high frequency is comparatively low because some solar light transmitted through a hole is lost in the air before it reaches the membrane structure. In addition, the size of a light interrupter must be greatly increased depending on the size of the thin metal plate. Therefore, it is substantially difficult to commercialize the technique.

SUMMARY OF THE INVENTION

Accordingly, the present invention has been made keeping in mind the above problems occurring in the prior art, and an object of the present invention is to provide a high-frequency acoustic wave generator using a pulsed thermal radiation beam that is configured such that when a pulse beam formed by a light interrupter is directly radiated onto a porous material having a woven net or steel scrubber shape, thin wires of the porous material repeatedly rapidly thermally-expand and contract, whereby air in the space between the wires is momentarily heated and cooled, and the expansion and contraction of air is directly transmitted to an air column formed just adjacent to the porous material. By virtue of the above structure, the efficiency of the generator according to the present invention is markedly improved compared to the conventional technique, and the productivity is also greatly enhanced.

Another object of the present invention is to provide a high-frequency acoustic wave generator using a pulsed thermal radiation beam that is configured to generate high-frequency (ultrasonic) waves from obtained acoustic waves and provide the acoustic waves to a variety of industrial fields including fields pertaining to sterilization, washing, etc.

In order to accomplish the above object, the present invention provides a high-efficiency acoustic wave generator using a pulsed thermal radiation beam, including: a focusing tube focusing solar light collected by a solar tracking reflector to form high-density light and emitting the focused solar light; a light interrupter including a circular disk and a rotating drive unit, the circular disk having a plurality of holes arranged at positions spaced apart from each other at regular intervals in a circumferential direction around the rotating drive unit so that solar light emitted from the focusing tube passes through the holes and thus is intermittently emitted, and a pulse beam is formed by intermittent solar light that has passed through one of the holes of the light interrupter; a housing body made of aluminum and having a hollow pipe structure, the housing body including: an open input end through which the pulse beam enters the housing body; a space formed behind the input end, the space forming an air column; and an open output end provided behind the space; a glass cover coupled to the open input end of the housing body; a porous material provided on a rear surface of the glass cover, the porous material including a wire configured such that when the wire is thermally-expanded by the pulse beam and thermally-contracted (repeatedly deformed), the air column in the space contracts and expands, thus generating sound; and a wave guide coupled to the open output end of the housing body, the wave guide transmitting the generated sound to a desired place of use.

The input end of the housing body may have a junction surface provided with a stepped protrusion, a surface of the porous material is formed to correspond to the junction surface, and a diameter of the space having the air column is ⅓ to ⅕ of a diameter of the input end.

The porous material may be disposed in the space of the housing body.

Preferably, the porous material is made of aluminum wires each of which has a diameter ranging from 0.1 μm to 1 μm and is superior in a light absorption coefficient, a thermal expansion coefficient and heat radiation performance.

Furthermore, the input end of the housing body has a smaller diameter than that of a cross-sectional area of a solar light beam passing through one of the holes of the light interrupter, whereby the thermal responsiveness can be maximized.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, the present invention will be described in detail with reference to the attached drawings.

Figure 1:
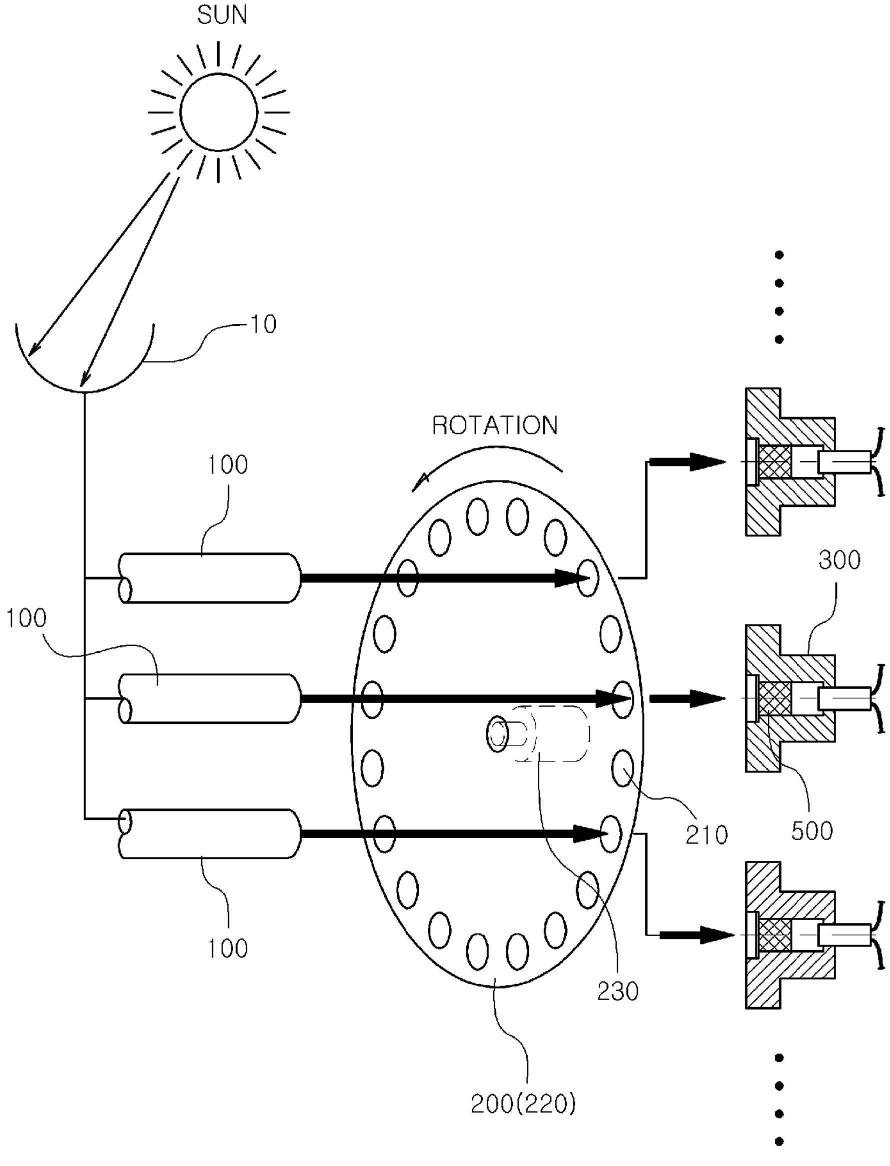
FIG. 1 is a schematic view showing the application of an acoustic wave generator according to the present invention.
Figure 2:
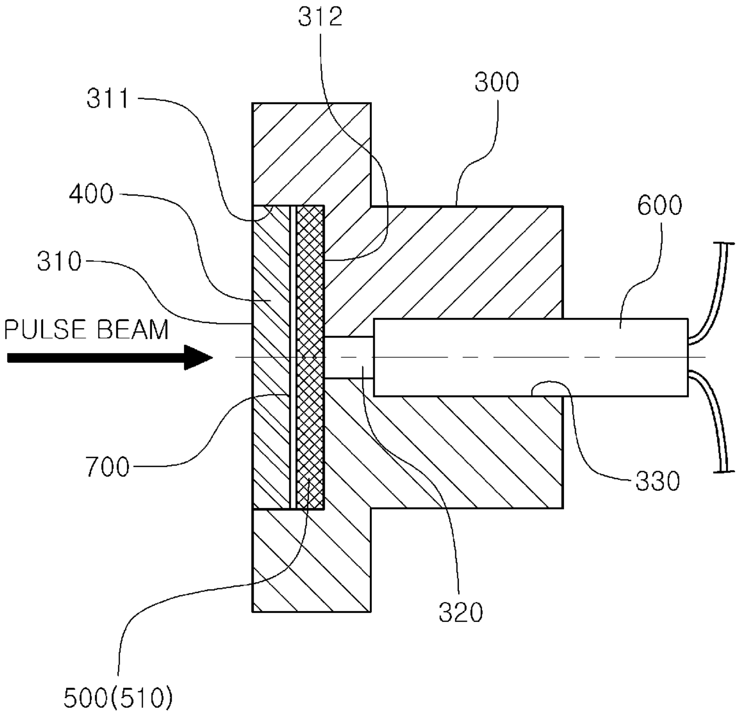
FIG. 2 is a sectional view illustrating an embodiment of the acoustic wave generator according to the present invention.
Figure 3:
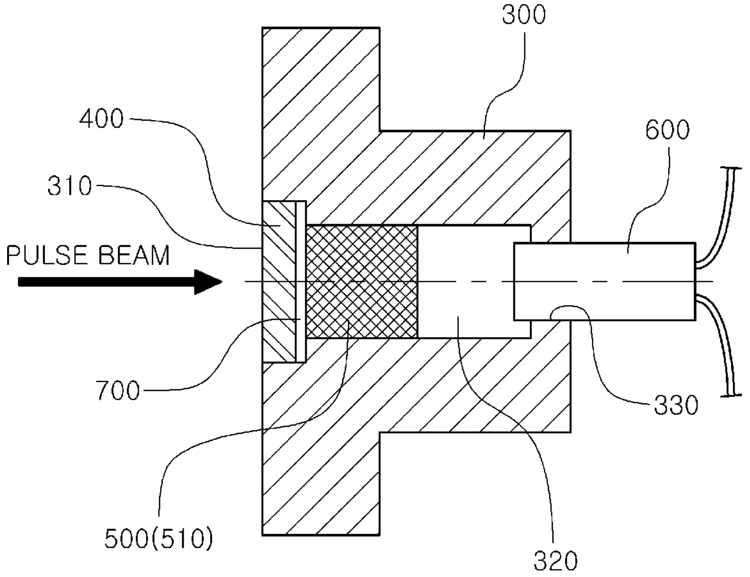
FIG. 3 is a sectional view illustrating another embodiment of the acoustic wave generator according to the present invention.

As shown in FIGS. 1 through 3, a high-efficiency acoustic wave generator according to the present invention includes a focusing tube 100, a light interrupter 200, a housing body 300 made of aluminum, and a porous material 500.

The focusing tube 100 focuses solar light collected by a solar tracking reflector to form high-density light and emits the focused light. The light interrupter 200 includes a circular disk 220 and a rotating drive unit 230. The circular disk 220 has a plurality of holes 210 that are arranged at positions spaced apart from each other at regular intervals in the circumferential direction around the rotating drive unit 230. Solar light emitted from the focusing tube 100 passes through the holes 210 so that the solar light is intermittently applied to the housing body 300.

As shown in FIG. 1, the holes 210 formed at regular intervals around the perimeter of the circular disk 220 of the light interrupter 200 cause light to intermittently pass through the circular disk 220, thus making a pulse beam. Depending on the number of holes 210 and the RPM of the circular disk 220, the frequency of the pulse beam is determined.

The housing body 300 is made of aluminum having high thermal responsiveness. A pulse beam formed by intermittently passing solar light through the holes 210 of the light interrupter 200 enters an open input end 310 of the housing body 300 having a hollow pipe shape. A space 320 forming an air column is formed behind the input end 310. An open output end 330 is formed behind the space 320.

A glass cover 400 is coupled to the open input end 310 of the housing body 300.

The porous material 500 is coupled to a rear surface of the glass cover 400. When wires 510 of the porous material 500 are thermally-expanded by pulse beams and thermally-contracted (repeatedly deformed), the air column in the space 320 also contracts and expands, thus generating sound.

A sealer 700 for airtightness is interposed between the glass cover 400 and the porous material 500. The reason for this is to maintain the space in the housing body 300 in a vacuum so that the thermal deformation of the wires 510 can rapidly and reliably conducted.

A wave guide 600 is coupled to the open output end of the housing body 300 and configured to transmit the generated sound to a desired place of use. Preferably, the wave guide comprises a microphone.

In an embodiment, the input end 310 of the housing body 300 has a junction surface 321 with a stepped protrusion 311. A surface of the porous material 500 is formed to correspond to the junction surface 312. The diameter of the space 320 having the air column is ⅓ to ⅕ of that of the input end 310.

That is, in the porous material 500 having a relatively large area corresponding to that of the junction surface of the input end 310, thermal deformation of contraction or expansion is comparatively large. On the other hand, thermal deformation of the space just adjacent to the porous material 500 is relatively small. Therefore, the amplitude of the air column can be comparatively large, whereby high frequency and high decibel of sound can be generated.

In another embodiment, the porous material 500 may be disposed in the space 320 of the housing body 300.

This embodiment forms a direct transmission structure between the porous material 500 and the air column, thus minimizing loss in the transmission structure.

Preferably, the porous material 500 is made of aluminum wires 510 each of which has a diameter ranging from 0.1 μm to 1 μm and is superior in a light absorption coefficient, a thermal expansion coefficient and heat radiation performance.

Furthermore, the input end 310 of the housing body 300 has a smaller diameter than that of a cross-sectional area of a solar light beam passing through one of the holes 210 of the light interrupter, whereby the thermal responsiveness can be maximized.

Preferably, the porous material 500 is coated with black to absorb as much solar light as possible.

Furthermore, the focusing tube 100 according to the present invention has a structure divided from the reflector into a plurality of focusing tubes 100, preferably, the number of which corresponds to the number of holes of the light interrupter 200. Connected to a converter, terminals (each of which includes the housing body, the glass cover, the porous material, the wave guide and the sealer) respectively matching with the focusing tubes are disposed at a side opposite to the focusing tubes based on the light interrupter 200. A variety of wavelengths of light caused due to the characteristics of solar light are synchronized (integrated) with each other by the converter so that the output power is collected.

As described above, a high-frequency acoustic wave generator using a pulsed thermal radiation beam according to the present invention is configured such that when a pulse beam formed by a light interrupter is directly radiated onto a porous material having a woven net or steel scrubber shape, thin wires of the porous material repeatedly rapidly thermally-expand and contract, whereby air in the space between the wires is momentarily heated and cooled, and the expansion and contraction of air is directly transmitted to an air column formed just adjacent to the porous material. By virtue of the above structure, the efficiency of the generator according to the present invention is markedly improved compared to the conventional technique, and the productivity is also greatly enhanced.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A high-efficiency acoustic wave generator using a pulsed thermal radiation beam, comprising:

a focusing tube focusing solar light collected by a solar tracking reflector to form high-density light and emitting the focused solar light;

a light interrupter including a circular disk and a rotating drive unit, the circular disk having a plurality of holes arranged at positions spaced apart from each other at regular intervals in a circumferential direction around the rotating drive unit so that the solar light emitted from the focusing tube passes through the holes and thus is intermittently emitted, and a pulse beam is formed by the intermittent solar light that has passed through one of the holes of the light interrupter;

a housing body made of aluminum and having a hollow pipe structure, the housing body including: an open input end through which the pulse beam enters the housing body; a space formed behind the input end, the space forming an air column; and an open output end provided behind the space;

a glass cover coupled to the open input end of the housing body;

a porous material provided on a rear surface of the glass cover, the porous material including a wire configured such that when the wire is thermally-expanded by the pulse beam and thermally-contracted, the air column in the space contracts and expands, thus generating sound; and a wave guide coupled to the open output end of the housing body, the wave guide transmitting the generated sound to a desired place of use.

2. The high-efficiency acoustic wave generator as set forth in claim 1, wherein the input end of the housing body has a junction surface provided with a stepped protrusion, a surface of the porous material is formed to correspond to the junction surface, and a diameter of the space having the air column is ⅓ to ⅕ of a diameter of the input end.

3. The high-efficiency acoustic wave generator as set forth in claim 1, wherein the porous material is disposed in the space of the housing body.

* * * * *